United States Patent
Brockbank et al.

(10) Patent No.: US 9,977,012 B2
(45) Date of Patent: May 22, 2018

(54) SELECT ON OF EXTRACELLULAR MATRIX COMPONENTS AND OR MATRICELLULAR PROTEINS FOR IMPROVED POST-CRYOPRESERVATION CELL VIABILITY AND RETENTION

(71) Applicant: LIFELINE SCIENTIFIC, INC., Itasca, IL (US)

(72) Inventors: Kelvin G. M. Brockbank, North Charleston, SC (US); Lia Campbell, North Charleston, SC (US)

(73) Assignee: LIFELINE SCIENTIFIC, INC., Itasca, IL (US)

( * ) Notice: Subject to any disclaimer, the term of this patent is extended or adjusted under 35 U.S.C. 154(b) by 96 days.

(21) Appl. No.: 14/523,114

(22) Filed: Oct. 24, 2014

(65) Prior Publication Data
US 2016/0116454 A1    Apr. 28, 2016

(51) Int. Cl.
| | |
|---|---|
| C12N 5/07 | (2010.01) |
| C12N 5/0775 | (2010.01) |
| A01N 1/00 | (2006.01) |
| G01N 33/50 | (2006.01) |
| A01N 1/02 | (2006.01) |
| F25D 25/00 | (2006.01) |
| F25D 31/00 | (2006.01) |
| C12N 5/00 | (2006.01) |

(52) U.S. Cl.
CPC ....... *G01N 33/5008* (2013.01); *A01N 1/0205* (2013.01); *A01N 1/0231* (2013.01); *A01N 1/0278* (2013.01); *C12N 5/0068* (2013.01); *F25D 25/00* (2013.01); *F25D 31/005* (2013.01); *C12N 2533/52* (2013.01); *C12N 2533/54* (2013.01)

(58) Field of Classification Search
CPC ... C12N 5/0068; C12N 5/0662–5/0668; A01N 1/0221; A01N 1/0231
See application file for complete search history.

(56) References Cited

U.S. PATENT DOCUMENTS 5,942,437 A * 8/1999 Sanberg ............... C12N 5/0619
424/93.7
6,596,531 B2    7/2003 Campbell et al.

FOREIGN PATENT DOCUMENTS

WO    2012/149484 A2    11/2012

OTHER PUBLICATIONS

BD Matrigel™ Basement Membrane Matrix Product Information Sheet, No Date. Retrieved from http://bd.com/resource.aspx?IDX=17841 on Jul. 7, 2016.*
Xu et al, Enhancement of Cell Recovery for Dissociated Human Embryonic Stem Cells after cryopreservation (2010). Biotechnology Progress, vol. 26, pp. 781-788.*
Xu et al "Effects of Cryopreservation on human mesenchymal stem cells attached to different substrates", Journal of Tissue Engineering and Regenerative Medicine, Aug. 2014 (first published online Jul. 19, 2012), vol. 8, pp. 664-672. (Year: 2014).*
Feb. 22, 2016 International Search Report issued in International Application No. PCT/US2015/057396.
Feb. 22, 2016 Written Opinion issued in International Application No. PCT/US2015/057396.
Ni et al., "Scalable culture and cryopreservation of human embryonic stem cells on microcarriers," Biotechnology Progress, American Institute of Chemical Engineers, US, vol. 25, No. 1, 2009, pp. 20-31.
Lu et al., "The Behaviors of Long-Term Cryopreserved Human Hepatocytes on Different Biomaterials," Artificial Organs, vol. 35, No. 3, 2011, pp. E65-E72.
Campbell et al-,"Cryopreservation of Adherent Cells on a Fixed Substrate," Recent Advances in Cryopreservation, 2014, Dr. Hideaki Yamashiro (ed.), InTech, DOI:10.5772/581618. Available from http://www.intechopen.com/books/recent-advances-in-cryopreservation/cryopresevation-of-adherent-cells-on-a-fixed-substrate.
Campbell et al., "Influence of the Extracellular Matrix on the Survival of Cryopreserved Adherent Cells," In Vitro Cellular & Developmental Biology-Animal, vol. 50, 2014, p. S28.
Underwood, "The Effect of Extracellular Matrix Molecules on the in Vitro Behavior of Bovine Endothelial Cells," Exp. Cell. Res. 205:311-319 (1993).
Armitage et al., "The Influence of Cooling Rate on Survival of Frozen Cells Differs in Monolayers and in Suspensions," Cryo-Letters 17: 213-218 (1996).
Ji et al., "Cryopreservation of Adherent Human Embryonic Stem Cells," Biotechnology and Bioengineering 88(3): 299-312 (2004).
Katkov et al., "DMSO-Free Programmed Cryopreservation of Fully Dissociated and Adherent Human Induced Pluripotent Stem Cells," Stem Cells International 2011, 2011:981606. doi: 10.4061/2011/981606. Epub Jun. 1, 2011.
Xu et al., "Effects of Osmotic and Cold Shock on Adherent Human Mesenchymal Stem Cells During Cryopreservation," J. Biotech. 162(2-3): 224-231 (2012).
Campbell et al., "Serum free solutions for the cryopreservation of cells," In Vitro Cell Dev. Biol., 43:269-275 (2007).
Campbell et al., "Cryopreservation of porcine aortic heart valve leaflet-derived myofibroblasts," Biopreservation and Biobanking, 8(4):211-217 (2010).

(Continued)

*Primary Examiner* — Allison M Fox
(74) *Attorney, Agent, or Firm* — Oliff PLC

(57) ABSTRACT

A method for cryopreservation of adherent cells attached to a substrate and a method for identifying one or more extracellular matrix (ECM) components and/or matricellular proteins that improves viability and retention of the cryopreserved cells on the substrate. The method for cryopreservation includes treating a substrate with at least one ECM component and/or adding at least one matricellular protein to the substrate or cell culture media, plating the cells on the treated substrate, and cryopreserving the cells. One or more ECM components and/or matricellular proteins that improves cell viability and retention can be identified by evaluating the cells that have been thawed from the cryopreservation temperature to determine cell viability and retention.

18 Claims, 9 Drawing Sheets

(56) References Cited

OTHER PUBLICATIONS

Campbell et al., "Culturing with Trehalose Produces Viable Endothelial Cells after Cryopreservation," Cryobiology, 64(3):240-244 (2012).
Hornung et al., "Cryopreservation of Anchorage-Dependent Mammalian Cells Fixed to Structured Glass and Silicon Substrates. Cryobiology," 33: 260-70 (1996).
McGann et al., "Cell-to-Cell and Cell-to-Surface Interactions Affect Responses During Cryopreservation," Transfusion 33(7): 611 (Abstract) (1993).
Morris et al., "Matricellular proteins and biomaterials," Matrix Biol., 37: 183-191 (2014).
Pasch et al., "Variation of the HES concentration for the Cryopreservation of Keratinocytes in Suspensions and in Monolayers," Cryobiology 41(2): 89-96 (2000).
Pasch et al., "Cryopreservation of Keratinocytes in a Monolayer," Cryobiology, 39(2): 158-168 (1999).
Frantz et al., "The extracellular matrix at a glance," J. Cell Sci. 123:4196-4200 (2010).
Malpique et al., "Cryopreservation of Adherent Cells: Strategies to Improve Cell viability and Function after Thawing," Tissue Engineering Part C Methods 15(3):373-386 (2009).
Underwood et al., "A Comparison of the Biological Activities of the Cell-Adhesive Proteins Vitronectin and Fibronectin," J. Cell. Sci. 93(Pt. 4): 641-649 (1989).
Gordon et al., "Role of the Cytoskeleton During Injury—Induced Cell Migration in Corneal Endothelium," Cell Motil. & Cytoskeleton, 16:47-57 (1990).
Gospodarowicz et al., "The Identification and Localization of Fibronectin in Cultured Corneal Endothelial Cells: Cell Surface Polarity and Physiological Implications," Exp. Eye Res. 29:485-509 (1979).
Gospodarowicz et al., "The Production and Localization of Laminin in Cultured Vascular and Corneal Endothelial Cells," J. Cell Physiol. 107:171-183 (1981).
Tseng et al., "Characterization of Collagens Synthesized by Cultured Bovine Corneal Endothelial Cells," J. Biol. Chem. 256(7):3361-3365 (1981).
Scott et al., "Investigation of the Attachment of Bovine Corneal Endothelial Cells to Collagens and Other Components of the Subendothelium," Exp. Cell Res. 144:472-478 (1983).
Singh et al., "Fibronectin and stem cell differentiation-lessons from chondrogenesis," J. Cell Sci. 125:3703-3712 (2012).
Bornstein et al., "Matricellular proteins: extracellular modulators of cell function," Curr. Opin. Cell Biol. 14:608-616 (2002).
Bornstein et al., "Matricellular proteins: an overview," J. Cell Commun. Signal. 3:163-165 (2009).
Frangogiannis, "Matricellular proteins in cardiac adaptation and disease," Physiol. Rev. 92:635-688 (2012).
Rixen et al., "Adhesion and Spreading of Corneal Endothelial Cells on Collagen Type I and IV in Vitro: A Model to Study Mechanisms of Endothelial Repair," Res. Exp. Med., 190:203-211 (1990).
Roberts, "Emerging functions of matricellular proteins," Cell Mol. Life Sci. 68(19):3133-3136 (2011).
Wong et al., "Matricellular proteins: priming the tumour microenvironment for cancer development and metastasis," Brit. J. Cancer, 108:755-761 (2013).
Campbell et al., "Cryopreservation of Adherent Smooth Muscle and Endothelial Cells with Disaccharides," In: Katkov I. (ed.) Current Frontiers in Cryopreservation. Croatia: In Tech (2012).

Campbell et al., "Development of Pancreas Storage Solutions: Initial Screening of Cytoprotective Supplements for β-cell Survival and Metabolic Status after Hypothermic Storage," Biopreservation and Biobanking 11(1): 12-18 (2013).
Taylor et al., "Comparison of Unisol with Euro-Collins Solution as a Vehicle Solution for Cryoprotectants," Transplantation Proceedings 33: 677-679 (2001).
Sicheri et al., "Ice-binding structure and Mechanism of antifreeze protein from winter flounder," Nature, 375:427-431, (1995).
DeVries, "Antifreeze glycopeptides and peptides: interactions with ice and water," Meth. Enzymol. 127:293-303 (1986).
Duman, "Antifreeze and ice nucleator proteins in terrestrial arthropods," Annual Rev. Physiol. 63:327-3257 (2001).
Holmstrup et al. "Dehydration and cold hardiness in the Arctic collembolan Onychiurus arcticus Tullberg 1879," J. Comp. Physiol. B 168: 197-203 (1998).
Kuiper et al., "Purification of antifreeze proteins by adsorption to ice," Biochem. Biophys. Res. Commun. 300(3): 645-648 (2003).
Miller, "Cold-hardiness strategies of some adult and immature insects overwintering in interior Alaska," Comp. Biochem. Physiol. 73A: 595-604 (1982).
Neven et al., "Purification and characterization of an insect hemolymph lipoprotein ice nucleator: evidence for the importance of phosphatidylinositol and apolipoprotein in the ice nucleator activity," J. Comp. Physiol. B 159: 71-82 (1989).
Sformo et al., "Deep supercooling, vitrification and limited survival to -100° C. in the Alaskan beetle Cucujus clavipes puniceus larvae," J. Exp. Biol. 213(3): 502-509 (2010).
Storey et al., "Freeze tolerance in animals," Physiol. Rev. 68: 27-84 (1988).
Storey et al., "Biochemical adaptation for cold hardiness in insects," Phil. Trans. R. Soc. Lond. B326: 635-54 (1990).
Walters et al., "Freeze tolerance in the Arctic Alaska Stonefly," J. Exp. Biol. 212: 305-12 (2009a).
Walters et al., "Cryoprotectant biosynthesis and the selective accumulation of threitol in the freeze tolerant Alaskan beetle, *Upis ceramboides*," J. Biol. Chem. 284: 16822-16831 (2009b).
Walters et al., "A Non-protein thermal hysteresis-producing xylomannan antifreeze in the freeze-tolerant Alaskan beetle, *Upis ceramboides*," Proc. Natl. Acad. Sci. 106, 20210-20215 (2009c).
Walters et al., "A thermal hysteresis-producing xylomannan glycolipid antifreeze associated with cold tolerance is found in diverse taxa," J. Comp. Physiol. B. 181(5): 631-40 (2011).
Wang et al., "Antifreeze proteins of the beetle *Dendroides canadensis* enhance one another's activities," Biochemistry 44: 10305-10312 (2005).
Worland et al., "Desiccation stress at subzero temperatures in polar terrestrial arthropods," J. Insect. Physiol. 49: 193-203 (2003).
Zachariassen et al., "Nucleating agents in the haemolymph of insects tolerant to freezing," Nature 262: 285-87 (1976).
Zachariassen, "Physiology of cold tolerance in insects," Physiol. Rev. 65: 799-832 (1985).
Vincent et al., "Effects of Cryoprotectants on Actin Filaments During the Cryopreservation of One-Cell Rabbit Embryos," Cryobiology, 27:9-23 (1990).
Roemer et al., "In Vitro Assay Systems for Inflammatory Cell-Mediated Damage to Interstitial Extracellular Matrix," In Vitro Toxicol., 7(2): 75-81 (1994).
Apr. 25, 2017 International Preliminary Report on Patentability issued in International Application No. PCT/US2015/057396.

\* cited by examiner

SELECT ON OF EXTRACELLULAR MATRIX COMPONENTS AND OR MATRICELLULAR PROTEINS FOR IMPROVED POST-CRYOPRESERVATION CELL VIABILITY AND RETENTION

BACKGROUND

The subject matter of this disclosure relates to a method of cryopreservation and subsequent thawing of adherent cells attached to a substrate. Also disclosed is a method of identifying one or more extracellular matrix (ECM) components and/or matricellular proteins that improve viability and retention of cells during and after thawing from a cryopreservation state.

The ongoing demand to reduce the number of animals used in research drives the development of in vitro assays, both cell and tissue based, that provide accurate toxicity data about various chemicals, compounds, and formulations. In 2009, the European Union banned the use of animals for testing of cosmetic ingredients. A ban on the use of animals for testing the toxicity of other types of compounds including pharmaceuticals and household chemicals will likely follow.

In response to this demand, cryopreservation of cells and tissues has been used to protect and preserve biological systems by cooling the cells and tissues to temperatures below the freezing point of water. Cryopreservation is generally carried out on cells in suspension and very few studies have examined cryopreservation of cells on a fixed substrate. Accordingly, the commonly used cryopreservation protocols that were developed for cell suspensions are typically applied to adherent cells on a fixed substrate as well, frequently resulting in cell detachment and membrane damage after cryopreservation. Survival of cells from the rigors of freezing and thawing in cryopreservation procedures is only attained by using appropriate cryoprotective agents. Thus, most research in cryobiology has been focused on finding and testing new types of cryoprotectants.

However, retention of cell attachment to the ECM, either natural or synthetic, after the rigors of freezing and thawing is crucial for the preservation of natural and engineered tissues and for other applications such as in vitro toxicology testing. Disruption of adhesive mechanisms inevitably has severe consequences; even reversible effects on the adhesion mechanism can be disastrous because spatial separation from the underlying ECM is sufficient to prevent reattachment.

Accordingly, there is a need for improved cryopreservation protocols for adherent cells. In particular, improved cell attachment and viability after warming the cells attached to a substrate from a cryopreserved state is desired.

SUMMARY

Disclosed herein is a method for cryopreservation of adherent cells attached to a substrate that improves cell viability and retention of the cryopreserved cells. The method includes treating a substrate with at least one ECM component and/or adding at least one matricellular protein to the substrate or cell culture media; plating the cells on the treated substrate; and cryopreserving the cells on the treated substrate by cooling the cells to a cryopreservation temperature.

Also disclosed is a method for identifying one or more ECM component and/or matricellular protein that improves viability and retention of cells on a substrate after thawing cells from a cryopreserved state. The method includes selecting cells of a specific cell type; treating substrates with one or more different ECM components and/or adding one or more matricellular protein to the substrate or cell culture media; plating the cells of the specific cell type on the treated substrates; cryopreserving the cells on the variously treated substrates by cooling the cells to a cryopreservation temperature; thawing the cells by first warming the cells from the cryopreservation temperature by exposing the treated substrate containing the cells to a first environment having a first warming temperature that is greater than the cryopreservation temperature, and then further warming the cells from the first warming temperature by exposing the cells to a second environment having a second warming temperature that is greater than the first warming temperature; evaluating the thawed cells to determine cell viability and retention; and identifying one or more ECM component and/or at least one matricellular component that improves viability and retention of the cells of the specific cell type after thawing the cells from the cryopreserved state.

DETAILED DESCRIPTION OF THE EMBODIMENTS

Figure 1A:
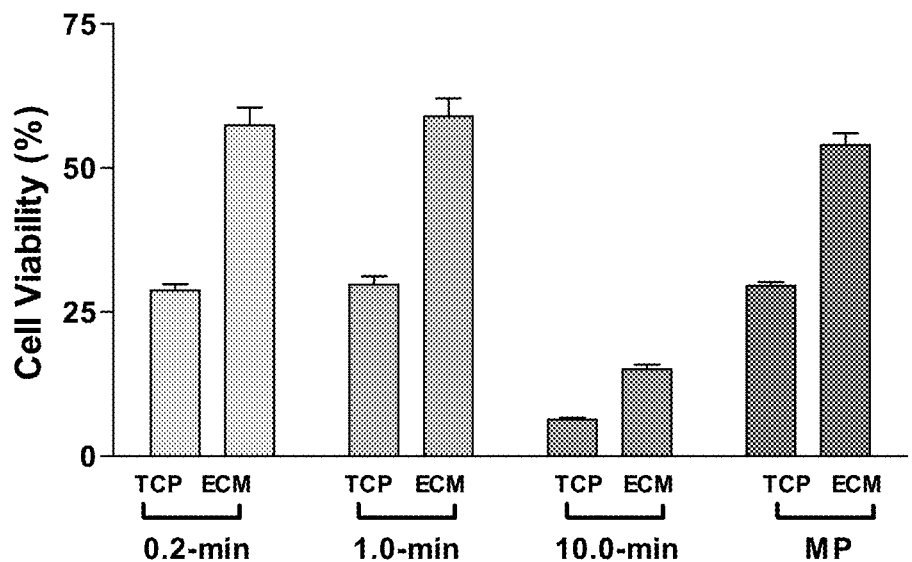
FIGS. 1A and 1B are bar graphs illustrating (A) cell viability and (B) DNA content (%) (i.e., cell retention) of adherent bovine corneal endothelial (BCE) cells on an ECM or tissue culture treated plastic (TCP) after cryopreservation at various cooling rates.

As used herein, the modifier "about" used in connection with a quantity is inclusive of the stated value and has the meaning dictated by the context. For example, it includes at least the degree of error associated with the measurement of the particular quantity. When used in the context of a range, the modifier "about" should also be considered as disclosing the range defined by the absolute values of the two endpoints. For example, the range "from about 2 to about 4" also discloses the range "from 2 to 4."

Unless otherwise expressly stated herein, the modifier "about" with respect temperatures (° C.) refers to the stated value or range of values as well as the stated value or range of values +/−1-4%.

Unless otherwise expressly stated herein, the modifier "about" with respect to cell viability and cell retention or attachment (%) refers to the stated value or range of values as well as the stated value or range of values +/−1-3%.

Unless otherwise expressly stated herein, the modifier "about" with respect to concentrations (μg/mL) refers to the stated value or range of values as well as the stated value or range of values +/−1-4%.

Unless otherwise expressly stated herein, the modifier "about" with respect to molarity (M) refers to the stated value or range of values as well as the stated value or range of values +/−1-2%.

Unless otherwise expressly stated herein, the modifier "about" with respect to cooling rates (° C./min) refers to the stated value or range of values as well as the stated value or range of values +/−1-3%.

As used herein, the term "room temperature" refers to a temperature of about 18° C. to about 25° C. at standard pressure. In various examples, room temperature may be about 18° C., about 19° C., about 20° C., about 21° C., about 22° C., about 23° C., about 24° C., or about 25° C.

The present methods relate to the cryopreservation, i.e., preservation by freezing, of adherent cells fixed on a substrate and the subsequent thawing, i.e., warming from a cryopreservation temperature, of the cells for a variety of applications such as in vitro toxicology testing. The term, "freezing" refers, for example, to temperatures below the freezing point of water, i.e., below 0° C. Cryopreservation typically involves freezing cells to temperatures well below freezing, e.g., to −80° C. or lower, more typically to −130° C. or lower. Any method of cryopreservation known to practitioners in the art may be used without limitation. The cryopreservation temperature may be less than −20° C., such as −80° C. or less, or −130° C. or less. The cryopreservation temperature may be about −20° C. to about −200° C., about −30 to about −175° C., about −50° C. to about −160° C., about −65° C. to about −150° C., about −75° C. to about −135° C., about −80° C. to about −130° C., about −90° C. to about −125° C., or about −100° C. to about −115° C. See, e.g., Armitage et al., "The Influence of Cooling Rate on Survival of Frozen Cells Differs in Monolayers and Suspensions," Cryo-Letters 17: 213-218 (1996).

The present methods are designed so that the cells are available for use immediately post-rewarming, eliminating the need for plating, expansion, and re-plating of cells. To this end, a two-stage warming protocol for warming cryopreserved adherent cells from a cryopreservation temperature has been developed. See, e.g., U.S. Pat. No. 6,596,531 to Campbell et al. ("Campbell '531"), which is incorporated herein by reference in its entirety and demonstrates that adherent cells can be cryopreserved as adherent differentiated cell monolayers in multi-well plates.

The present methods are directed to the cryopreservation of adherent cells, e.g., BCE cells and hMSCs, attached to a substrate. See, e.g., Ji et al., "Cryopreservation of Adherent Human Embryonic Stem Cells," Biotechnology and Bioengineering 88(3): 299-312 (2004); Katkov et al., "DMSO-Free Programmed Cryopreservation of Fully Dissociated and Adherent Human Induced Pluripotent Stem Cells," Stem Cells International 2011, 2011:981606. doi: 10.4061/2011/981606. Epub 2011 Jun. 1; and Xu et al., "Effects of Osmotic and Cold Shock on Adherent Human Mesenchymal Stem Cells During Cryopreservation," J. Biotech. 162(2-3): 224-231 (2012).

Any suitable substrate may be used without limitation. For example, the cells may be attached to tissue culture plastic (TCP) that constitutes the surface of a microtiter plate having multiple wells (i.e., multiwell plates), collagen gels, natural matrices, or synthetic materials. The attachment of cells to a substrate is known in the art. See, e.g., Campbell et al., "Serum free solutions for the cryopreservation of cells," In Vitro Cell Dev. Biol., 43:269-275 (2007); Campbell et al., "Cryopreservation of porcine aortic heart valve leaflet-derived myofibroblasts," Biopreservation and Biobanking, 8(4):211-217 (2010); Campbell et al., "Culturing with Trehalose Produces Viable Endothelial Cells after Cryopreservation," Cryobiology, 64(3):240-244 (2012); Hornung et al., "Cryopreservation of Anchorage-Dependent Mammalian Cells Fixed to Structured Glass and Silicon Substrates. Cryobiology," 33: 260-70 (1996); McGann et al., "Cell-to-Cell and Cell-to-Surface Interactions Affect Responses During Cryopreservation," Transfusion 33(7): 611 (1993); Ohno, "A Simple Method for In Situ Freezing of Anchorage-Dependent Cells," in: A Doyle, J B Griffiths, D G Newell (eds.), Cell and Tissue Culture: Laboratory Procedures, Chichester: John Wiley and Sons (1994); Pasch et al., "Variation of the HES concentration for the Cryopreservation of Keratinocytes in Suspensions and in Monolayers," Cryobiology 41(2): 89-96 (2000); and Pasch et al., "Cryopreservation of Keratinocytes in a Monolayer," Cryobiology, 39(2): 158-168 (1999), each of which is incorporated herein by reference in its entirety and demonstrates the successful viability and cell attachment of adherent cells to TCP.

The present methods are directed to promoting and improving the viability and attachment of cells during cryopreservation by treating the substrates with an ECM or one or more ECM components. The ECM is a dynamic structural niche that provides the structural framework for tissues and is also intimately involved in cell processes such as signaling, differentiation, proliferation, adhesion, polarity, and survival. See, e.g., Frantz et al., "The extracellular matrix at a glance," J. Cell Sci. 123:4196-4200 (2010), which discloses that the ECM plays an important role in the ultimate health of cells.

The phrases, "improved cell viability" or "improved viability," refer, for example, to a cell viability (%) of at least 60%, such as 80% or more. The improved cell viability (%) may be 65% or more, 67% or more, 70% or more, 73% or more, 75% or more, 77% or more, 80% or more, 83% or more, 85% or more, 87% or more, 90% or more, 93% or more, 95% or more, 97% or more, 98% or more, or 99% or more. Likewise, the terms, "cell retention," "retention," "cell attachment," or "attachment," refer, for example, to a measurement of DNA content, which may be used as an indicator of cell number. The phrases, "improved cell retention," "improved retention," "improved cell attachment," or "improved attachment," refer, for example, to a DNA content (%) of at least 80%, 81% or more, 82% or more, 83% or more, 84% or more, 85% or more, 87% or more, 89% or more, 90% or more, 92% or more, 95% or more, 96% or more, 97% or more, 98% or more, or 99% or more. See, e.g., Malpique et al., "Cryopreservation of Adherent Cells: Strategies to Improve Cell viability and Function after Thawing," Tissue Engineering Part C Methods 15(3):373-386 (2009).

Figure 1B:
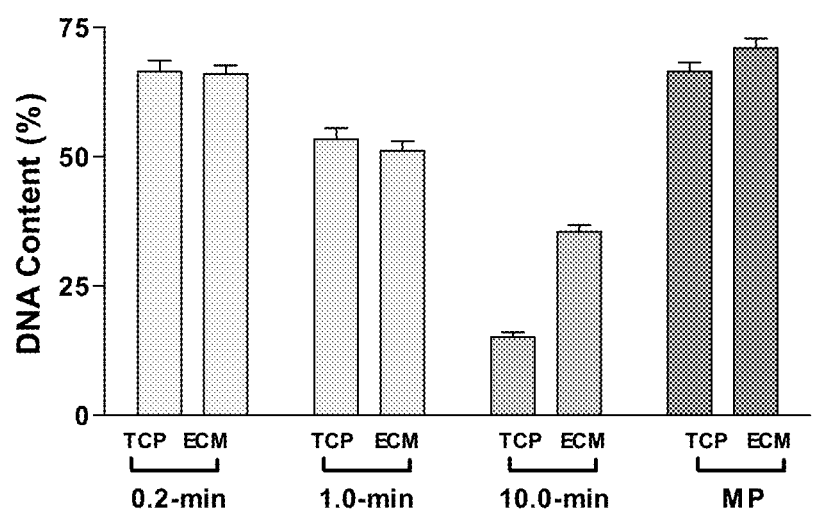
Figure 2A:
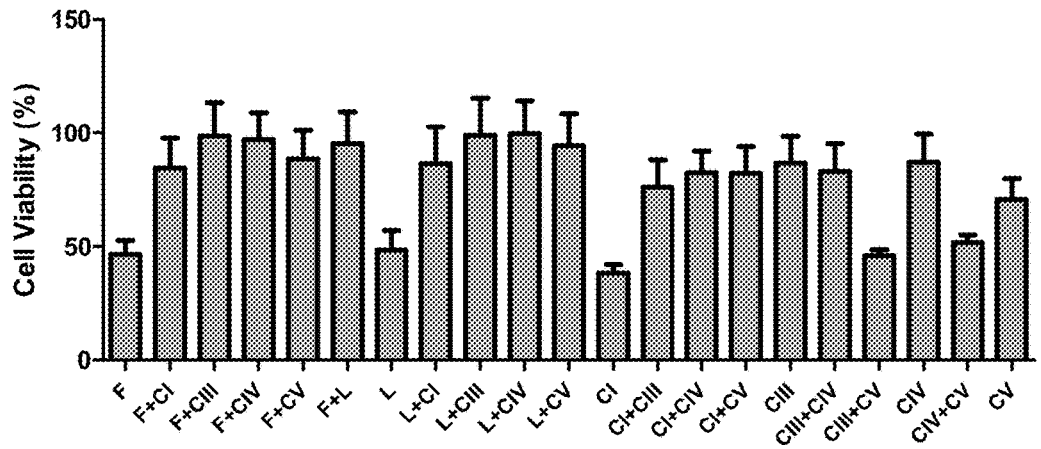
FIGS. 2A-2D are bar graphs illustrating cell viability of adherent BCE cells after cryopreservation with (A) single and pairs of ECM components, (B) groups of 3 ECM components, (C) groups of 4 ECM components, and (D) groups of 5 ECM components.
Figure 2B:
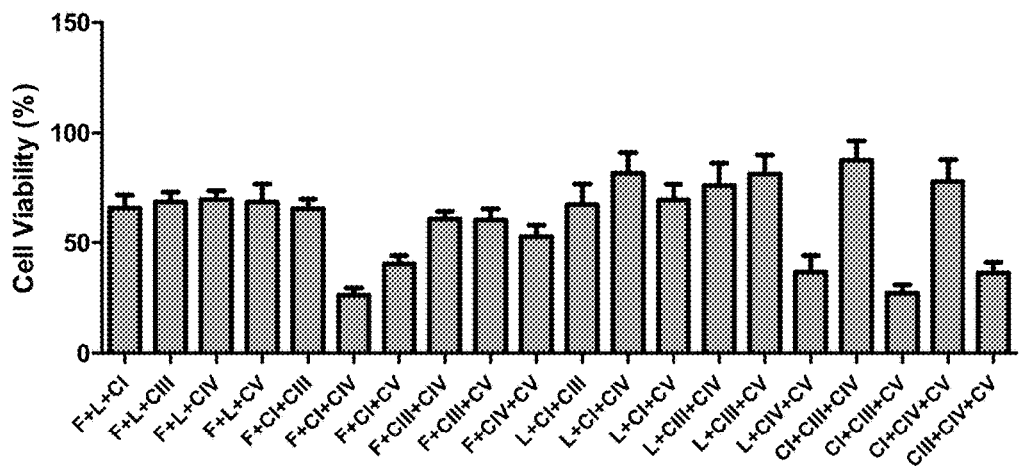
Figure 2C:
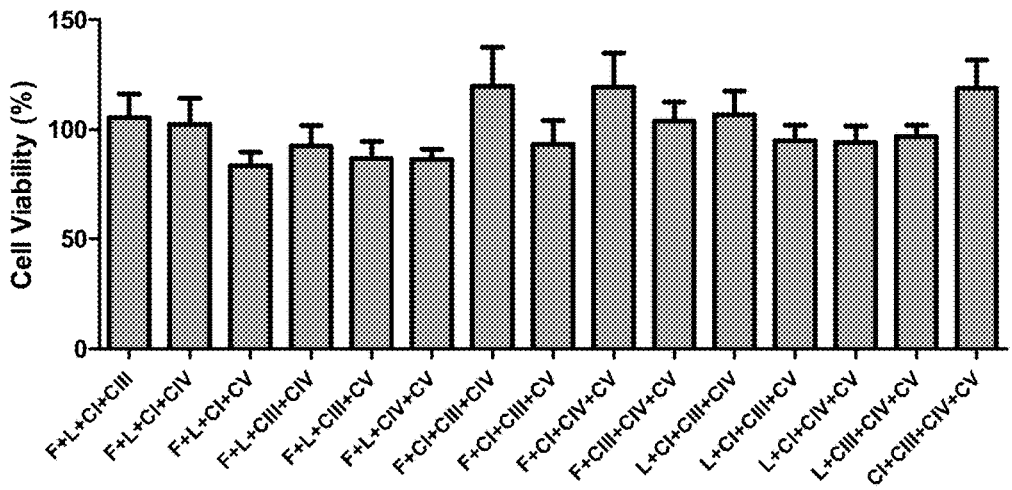
Figure 2D:
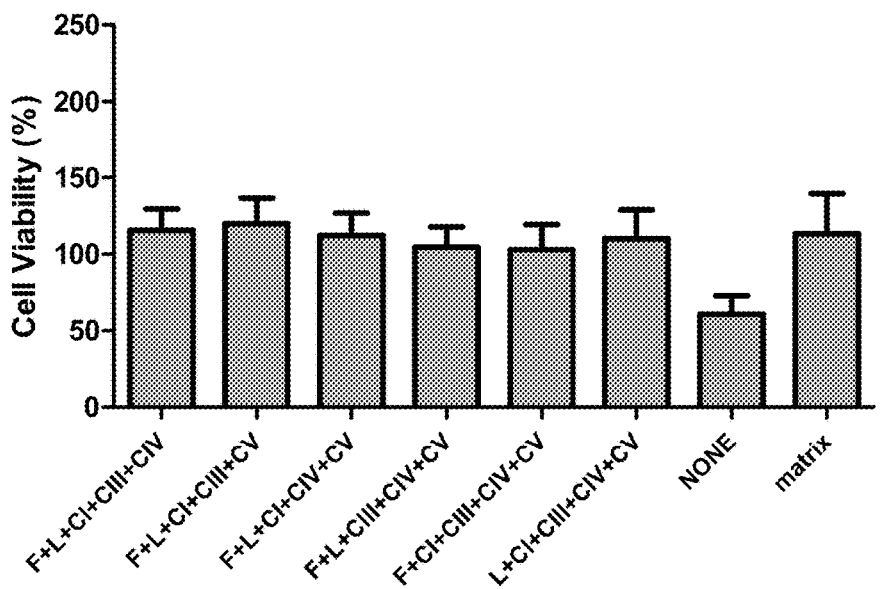
Figure 3A:
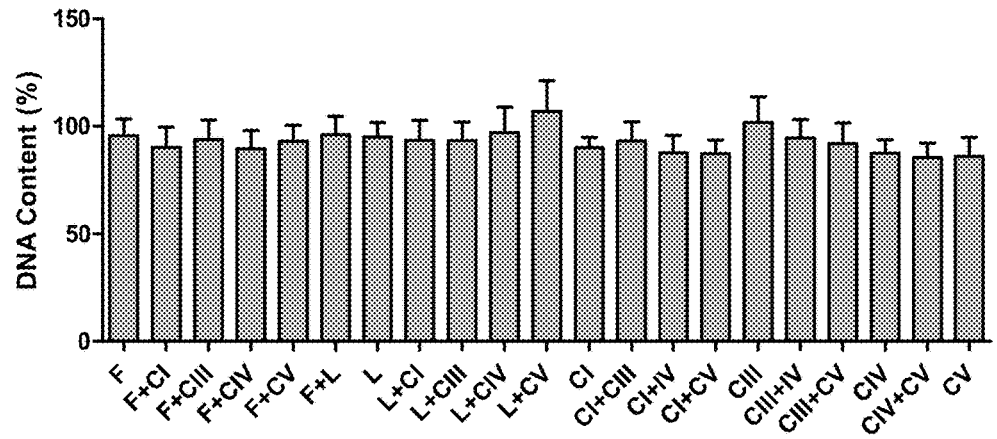
FIGS. 3A-3D are bar graphs illustrating DNA content (%) (i.e., cell retention) of adherent BCE cells after cryopreservation with (A) single and pairs of ECM components, (B) groups of 3 ECM components, (C) groups of 4 ECM components, and (D) groups of 5 ECM components.
Figure 3B:
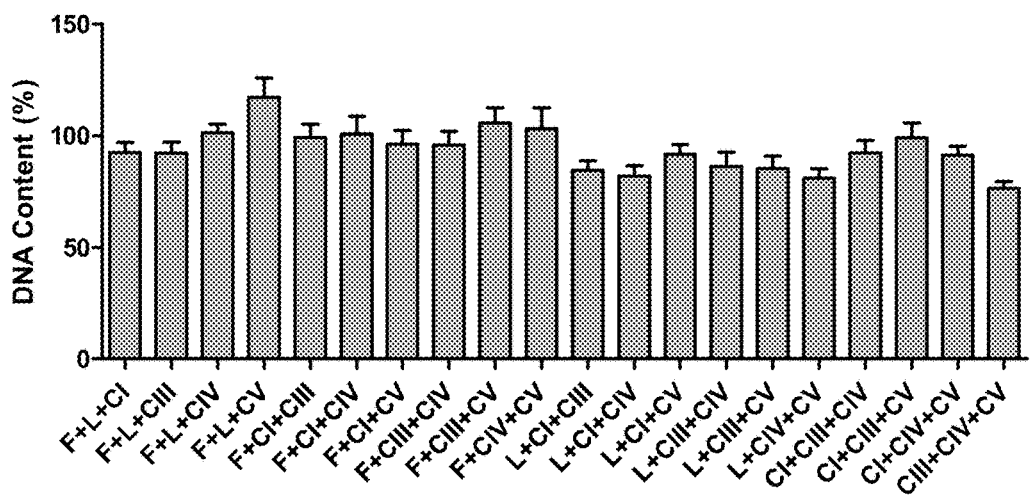
Figure 3C:
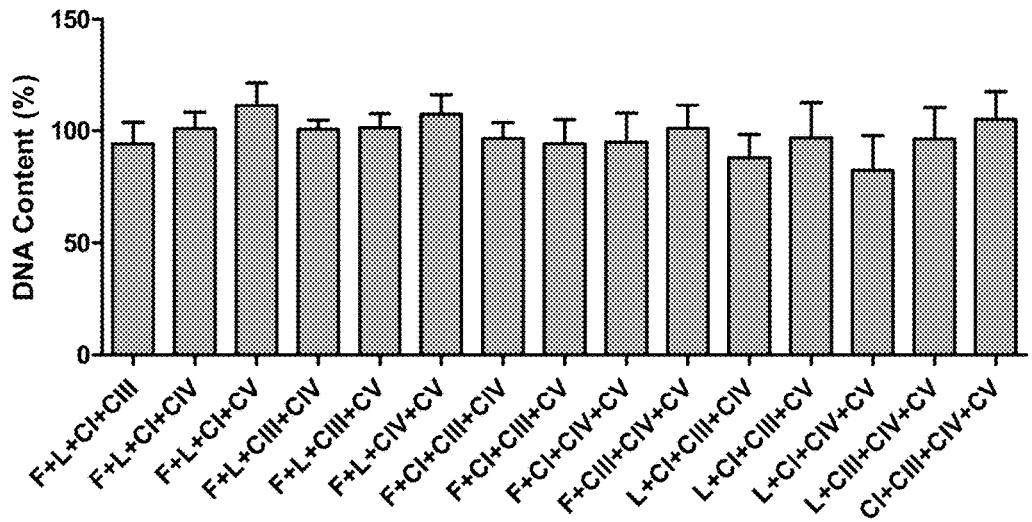
Figure 3D:
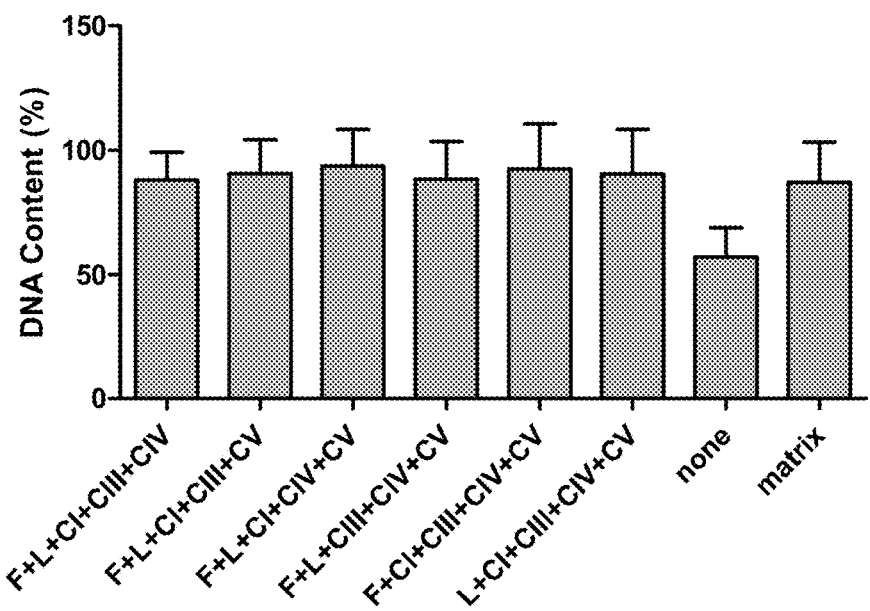
Figure 4A:
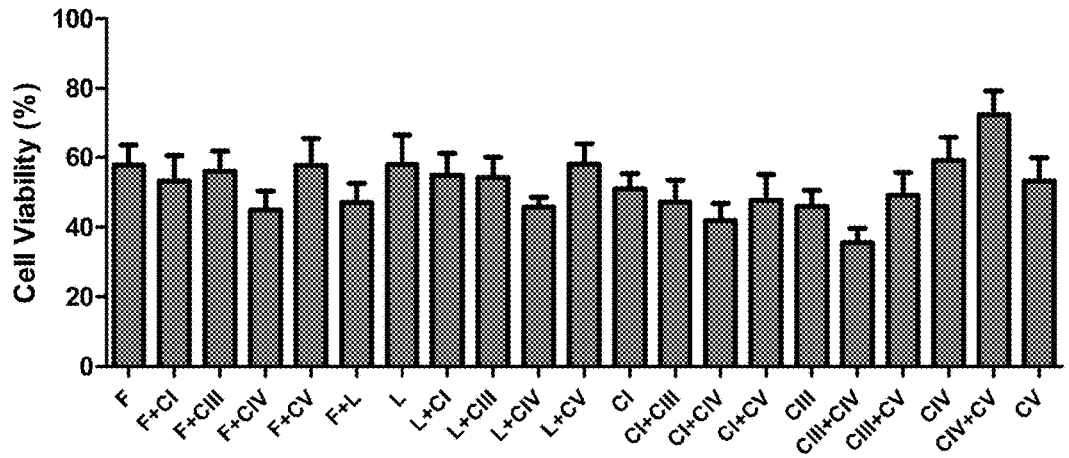
FIGS. 4A-4D are bar graphs illustrating cell viability of adherent human mesenchymal stem cells (hMSCs) after cryopreservation with (A) single and pairs of ECM components, (B) groups of 3 ECM components, (C) groups of 4 ECM components, and (D) groups of 5 ECM components.
Figure 4B:
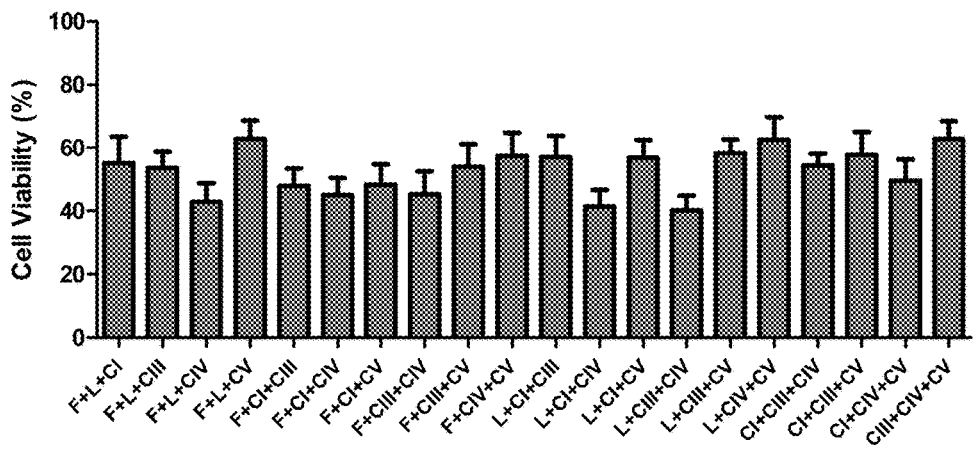
Figure 4C:
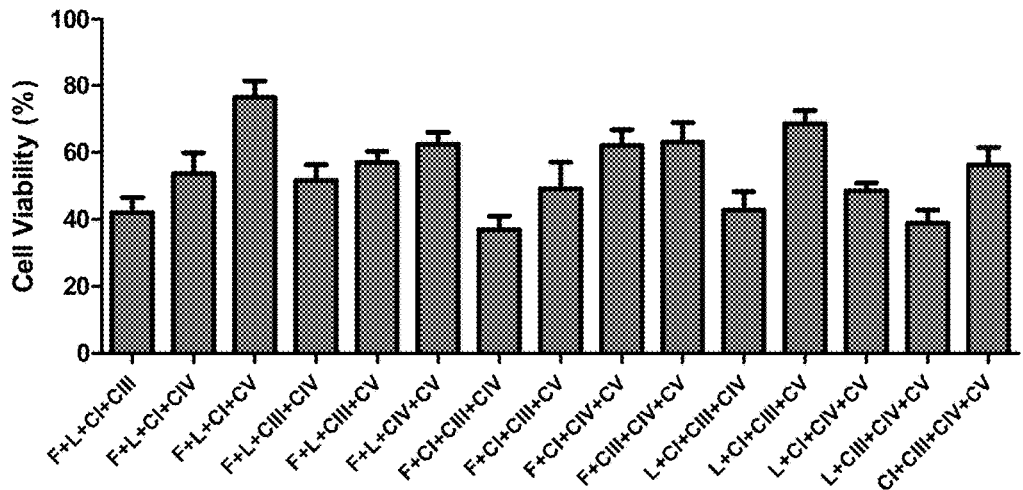
Figure 4D:
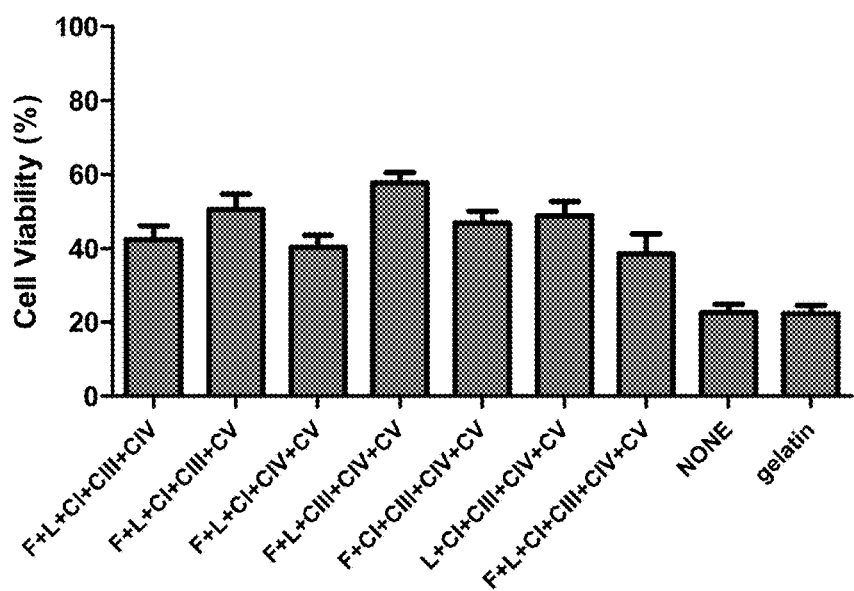

As illustrated in FIG. 1, attachment of the cells to an ECM rather than TCP improves cell viability and retention during and after cryopreservation. The presence of a fully formed and organized ECM provides a surface that more closely resembles the cells' native environment. Therefore, cell attachment may be affected less by the cryopreservation process. Additionally, the composition of the ECM may influence the ability of the cells to remain attached during cryopreservation. Furthermore, by cryopreserving the cells with an ECM, the cells are in a configuration that may be more conducive to their overall health and may improve their endurance and resilience in response to freezing temperatures.

Some embodiments relate to the cryopreservation of adherent cells on a fully formed ECM. Other embodiments relate to the cryopreservation of adherent cells with certain ECM components to promote attachment of cells during cryopreservation and to provide a more natural environment for the cells after they have been rewarmed from a cryopreservation state prior to use. Treating substrates with ECM components may involve coating ECM components on the cell substrate.

The ECM components may include any ECM component known in the art. For instance, it is known in the art that the attachment of cells to the ECM substratum is mediated via junctional complexes (adhesion plaques). These junctional complexes involve specific adhesion receptors, many of which belong to a large superfamily of homologous matrix receptors called integrins that, for the most part, recognize the Arg-Gly-Asp (RGD) tripeptide sequence in the extracellular proteins they bind. Some cells use other apparently unrelated, transmembrane glycoproteins in binding to collagen, and many cells have integral membrane proteoglycans that link cells directly to the ECM. See, e.g., Rixen et al., "Adhesion and Spreading of Corneal Endothelial Cells on Collagen Type I and IV In Vitro: A Model to Study Mechanisms of Endothelial Repair," Res. Exp. Med., 190: 203-211 (1990).

Under culture conditions, the initial attachment of a variety of cell types such as bovine corneal endothelial cells to tissue culture polystyrene may be dependent upon the adsorption of cell-adhesion glycoproteins, such as fibronectin and/or vitronectin, onto the culture surface. See, e.g., Underwood et al., "A Comparison of the Biological Activities of the Cell-Adhesive Proteins Vitronectin and Fibronectin," J. Cell. Sci. 93(Pt. 4): 641-649 (1989). Such cell-adhesion proteins may be pre-coated onto the polymer in a purified form prior to cell seeding; they may also adsorb onto the culture surface from the serum used to supplement the culture medium; or they may be synthesized by the cells and deposited onto the plastic surface.

Endogenous proteins have been reported to contribute, at least in part, to the attachment of cells to the synthetic substrate in the absence of serum-derived proteins such as fibronectin or vitronectin. Any newly identified or well-known endogenous proteins and cell adhesion proteins may be used. See, e.g., Gordon et al., "Role of the Cytoskeleton During Injury—Induced Cell Migration in Corneal Endothelium," Cell Motil. & Cytoskeleton, 16:47-57 (1990). Proteoglycan-mediated interactions may promote the organization of actin filaments in the attaching cell. The dynamic effects of actin involve the action of actin-binding proteins, which modulate actin filament length and association, and depend on the equilibrium between globular and filamentous actin. This is influenced by temperature, pH, ionic strength and the presence of organic solvents, all of which are factors in cryopreservation. Therefore, actin-binding proteins may be used as ECM proteins in the present methods.

BCE cells produce a number of ECM proteins to establish a mature matrix, including fibronectin, laminin, and collagen types I, III, IV, and V. Fibronectin and laminin are differentially expressed by isolated cells and cells in a monolayer. Similarly, the different collagen types are also not expressed equally with collagen III predominating. See, e.g., Gospodarowicz et al., "The Identification and Localization of Fibronectin in Cultured Corneal Endothelial Cells: Cell Surface Polarity and Physiological Implications," Exp. Eye Res. 29:485-509 (1979); Gospodarowicz et al., "The Production and Localization of Laminin in Cultured Vascular and Corneal Endothelial Cells," J. Cell Physiol. 107:171-183 (1981); and Scheffer et al., "Characterization of Collagens Synthesized by Cultured Bovine Corneal Endothelial Cells," J. Biol. Chem. 256(7):3361-3365 (1981). For example, laminin, which is largely produced prior to the formation of a monolayer, is followed by a decrease in protein production, and may not facilitate adhesion during cryopreservation like fibronectin whose production does not change with cell density. In addition, combinations of components may prove to be a better matrix for maintaining attachment and viability. For instance, fibronectin has been shown to facilitate the attachment of bovine corneal endothelial cells to collagens in the matrix. See, e.g., Scott et al., "Investigation of the Attachment of Bovine Corneal Endothelial Cells to Collagens and Other Components of the Subendothelium," Exp. Cell Res. 144:472-478 (1983).

hMSCs also produce ECM proteins, including fibronectin, laminin, and collagen types I, III, IV, and V, and can be greatly influenced by the ECM niche in which they are present. The ECM composition influences how and in what lineage direction mesenchymal stem cells will differentiate, which needs to be considered when developing ECM coatings for stem cells that will be cryopreserved on plates. See, e.g., Singh et al., "Fibronectin and stem cell differentiation-lessons from chondrogenesis," J. Cell Sci. 125:3703-3712 (2012).

The substrate may be treated with ECM components that include one or more of: fibronectin, laminin, collagen I, collagen III, collagen IV, and collagen V. The substrate may be treated with ECM components at a concentration of about 0.5 to about 25 µg/mL, such as about 1 to about 15 µg/mL, or about 1 to about 10 µg/mL. The substrate may be treated with ECM components at a concentration of about 0.75 to about 20 µg/mL, about 2 to about 20 µg/mL, about 2 to about 15 µg/mL, about 5 to about 10 µg/mL, about 5 to about 12 µg/mL, about 5 to about 15 µg/mL, about 5 to about 18 µg/mL, about 5 to about 20 µg/mL, about 5 to about 22 µg/mL, about 7 to about 20 µg/mL, about 7 to about 15 µg/mL, about 7 to about 10 µg/mL, about 10 to about 25 µg/mL, about 10 to about 20 µg/mL, about 10 to about 15 µg/mL, about 15 to about 25 µg/mL, or about 15 to about 20 µg/mL.

When the cells to be cryopreserved are bovine corneal endothelial cells, the substrate may be treated with ECM components that may include one, two, three, four, five, or six of: fibronectin, laminin, collagen I, collagen III, collagen IV, and collagen V. Exemplary combinations of ECM components include: fibronectin, collagen I, and collagen V; fibronectin, laminin, collagen I, and collagen IV; fibronectin, collagen III, collagen IV, and collagen V; or collagen I, collagen III, collagen IV, and collagen V.

When the cells to be cryopreserved are human mesenchymal stem cells, the ECM component may be one or more protein including fibronectin, laminin, collagen I, collagen II, collagen IV, and collagen V. Exemplary combinations of ECM components may include: fibronectin, collagen IV, and/or collagen V; fibronectin, collagen I, and collagen V; collagen IV and collagen V; fibronectin, laminin, and collagen V; laminin, collagen IV, and collagen V; collagen III, collagen IV, and collagen V; and laminin, collagen I, collagen III, and collagen V.

In addition to ECM components, matricellular proteins may be added to the substrate or they may be added to cell culture media. In recent years, the function and importance of matricellular proteins has been revealed. Although, these proteins are found in the ECM, they do not play a significant role in the maintenance of the structure of the matrix. Instead, they are involved in modulating cell function. Matricellular proteins modulate cell functions by interacting with cell-surface receptors, hormones and other effector molecules including the ECM. They are secreted and present in the extracellular environment but do not play a structural role like the traditional ECM proteins. Although more prominent during development, they are still present in adults, particularly at sites of injury. They perform a wide variety of functions that are dictated by the context in which they are present. Any of the known matricellular proteins or matricellular proteins discovered in the future may be used in the present method. See, e.g., Bornstein et al., "Matricellular proteins: extracellular modulators of cell function," Curr. Opin. Cell Biol. 14:608-616 (2002); Bornstein et al., "Matricellular proteins: an overview," J. Cell Commun. Signal. 3:163-165 (2009); Frangogiannis, "Matricellular proteins in cardiac adaptation and disease," Physiol. Rev. 92:635-688 (2012); Morris et al., "Matricellular proteins and biomaterials," Matrix Biol. Mar. pii:S0945-053X(14)00051-1. Doi: 10.1016/j.matbio.2014.03.002 (2014); Roberts, "Emerging functions of matricellular proteins," Cell Mol. Life Sci. 68(19):3133-3136 (2011); Wong et al., "Matricellular proteins: priming the tumour microenvironment for cancer development and metastasis," Brit. J. Cancer, 108: 755-761 (2013). Most studies to date have investigated the various functions of matricellular proteins using knockout mice, while few studies have evaluated these proteins in vitro.

The ability of the matricellular proteins to influence cell behavior may be used to promote viability and cell attachment in an in vitro system. As such, the substrates may be treated with one or more matricellular protein, alone or in combination with ECM components. That is, the method may also include the addition of matricellular proteins to cell substrates or culture media. Suitable matricellular proteins include thrombospondin-1, tenascin-C, tenascin-X, SPARC (secreted protein, acidic and rich in cysteine), periostin, CCN-1, and osteopontin.

Matricellular proteins may be used in concentrations of about 0 to about 5 µg/mL. The matricellular proteins may be used in concentrations of about 0.25 to about 5 µg/mL, about 0.5 to about 5 µg/mL, about 0.75 to about 5 µg/mL, about 1 to about 5 µg/mL, about 2 to about 5 µg/mL, about 3 to about 5 µg/mL, about 4 to about 5 µg/mL, about 0 to about 4 µg/mL, about 0 to about 3 µg/mL, about 0 to about 2 µg/mL, about 0 to about 1 µg/mL, about 0.5 to about 4 µg/mL, about 0.5 to about 3 µg/mL, about 1 to about 4 µg/mL, about 1 to about 3 µg/mL, or about 1 to about 2 µg/mL.

The cells may be further protected prior to cryopreservation by incubation with disaccharides, such as trehalose (Campbell et al., Method for treatment of cellular materials with sugars prior to preservation. U.S. Pat. No. 7,270,946 issued on Sep. 18, 2007).

The cells may be further protected during cryopreservation by being contacted with a cryopreservation composition prior to freezing to the cryopreservation temperature. Being contacted with the cryopreservation composition means that the cells are made to be in contact in some manner with the cryopreservation composition so that during the reduction of temperature to the cryopreservation temperature, the cells are protected by the cryopreservation composition. For example, the cells may be contacted with the cryopreservation composition by filling the appropriate wells of a plate to which the cells to be protected are attached.

The cells to be cryopreserved may also be in contact with a freezing-compatible pH buffer comprised most typically of at least a basic salt solution, an energy source (for example, glucose), and a buffer capable of maintaining a neutral pH at cooled temperatures. Well known such materials include, for example, Dulbecco's Modified Eagle Medium (DMEM). This material may also be included as part of the cryopreservation composition. See, e.g., Campbell et al., "Cryopreservation of Adherent Smooth Muscle and Endothelial Cells with Disaccharides," In: Katkov I. (ed.) Current Frontiers in Cryopreservation. Croatia: In Tech (2012); and Campbell et al., "Development of Pancreas Storage Solutions: Initial Screening of Cytoprotective Supplements for β-cell Survival and Metabolic Status after Hypothermic Storage," Biopreservation and Biobanking 11(1): 12-18 (2013).

The cryopreservation composition may comprise any cryoprotective materials known in the art. Known cryoprotectant compounds include acetamide, agarose, alginate, 1-analine, albumin, ammonium acetate, butanediol, chondroitin sulfate, chloroform, choline, dextrans, diethylene glycol, dimethyl acetamide, dimethyl formamide, dimethyl sulfoxide (DMSO), erythritol, ethanol, ethylene glycol, formamide, glucose, glycerol, α-glycerophosphate, glycerol monoacetate, glycine, hydroxyethyl starch, inositol, lactose, magnesium chloride, magnesium sulfate, maltose, mannitol, mannose, methanol, methyl acetamide, methylformamide, methyl ureas, phenol, pluronic polyols, polyethylene glycol, polyvinylpyrrolidone, proline, propylene glycol, pyridine N-oxide, ribose, serine, sodium bromide, sodium chloride, sodium iodide, sodium nitrate, sodium sulfate, sorbitol, sucrose, trehalose, triethylene glycol, trimethylamine acetate, urea, valine, xylose, etc.

The cryoprotectant compounds may be present in the cryopreservation composition in an amount of from, for example, about 0.05 M to about 6 M, about 0.1 to about 3 M, about 0.25 to about 6 M, about 1 to about 6 M, about 2 to about 6 M, about 3 to about 6 M, about 4 to about 6 M, about 5 to about 6M, about 0.25 to about 1 M, about 0.25 to about 2 M, about 0.25 to about 3 M, about 0.25 to about 4 M, about 0.25 to about 5 M, about 1 to about 4 M, about 1 to about 3 M, about 1 to about 2 M, about 3 to about 5 M, about 2 to about 4 M, about 0.5 to about 6 M, about 0.5 to about 5 M, about 0.5 to about 4 M, about 0.5 to about 3 M, about 0.5 to about 2 M, or about 0.5 to about 1M.

The cryoprotectant composition may include at least one cyclohexanediol (CHD) compound, for example the cis or trans forms of 1,3-cyclohexanediol (1,3CHD) or 1,4-cyclohexanediol (1,4CHD), or racemic mixtures thereof, as a cryoprotectant compound.

The CHD compound may be present in the cryopreservation composition in an amount of from, for example, about 0.05 to about 2 M, about 0.1 M to about 1 M, about 0.1 to about 2 M, about 0.1 to about 1 M, about 0.1 to about 1.5 M, about 0.1 to about 0.5 M, about 0.1 to about 0.25 M, about 1 to about 2 M, about 1.5 to about 2 M, about 0.75 to about 2 M, about 0.75 to about 1.5 M, about 0.75 to about 1 M, about 0.05 to about 1 M, about 0.05 to about 0.75 M, about 0.05 to about 0.5 M, or about 0.05 to about 0.1 M. The cryopreservation composition also may include a solution well suited for organ storage of cells, tissues and organs. The solution may include the buffers discussed above. The solution may be, for example, the EuroCollins Solution, which is composed of dextrose, potassium phosphate monobasic and dibasic, sodium bicarbonate, and potassium chloride. See, e.g., Taylor et al., "Comparison of Unisol with Euro-Collins Solution as a Vehicle Solution for Cryoprotectants," Transplantation Proceedings 33: 677-679 (2001).

The cryopreservation composition may include both at least one CHD compound and at least one additional cryoprotectant compound.

Still further, the cryopreservation composition may also include an anti-freeze protein/peptide (AFP) or anti-freeze glycolipid (AFGL). AFPs also include anti-freeze glycoproteins (AFGPs) and insect anti-freeze, or "thermal hysteresis" proteins, (THPs). The recently discovered AFGLs have been observed in insects and plants. Naturally occurring AFPs are believed to be able to bind to the prism face of developing ice crystals, thereby altering their formation. For the fishes and insects in which these proteins occur, it means a depression of their freezing point so they are able to survive under conditions that would normally cause their body fluids to freeze. Any newly discovered or well-known AFPs may be used in the present method in this regard. See, e.g., Sicheri and Yang, Nature, 375:427-431, (1995), describing eight such proteins; DeVries, "Antifreeze glycopeptides and peptides: interactions with ice and water," Meth. Enzymol. 127:293-303 (1986); Duman, "Antifreeze and ice nucleator proteins in terrestrial arthropods," Annual Rev. Physiol. 63:327-3257 (2001); Holmstrup et al. "Dehydration and cold hardiness in the Arctic collembolan *Onychiurus arcticus*," J. Comp. Physiol. B 168: 197-203 (1998); Kuiper et al., "Purification of antifreeze proteins by adsorption to ice," Biochem. Biophys. Res. Commun. 300(3): 64-68 (2003); Miller, "Cold-hardiness strategies of some adult and immature insects overwintering in interior Alaska," Comp. Biochem. Physiol. 73A: 595-604 (1982); Neven et al., "Purification and characterization of an insect hemolymph lipoprotein ice nucleator: evidence for the importance of phosphatidylinositol and apolipoprotein in the ice nucleator activity," J. Comp. Physiol. B 159: 71-82 (1989); Sformo et al., "Deep supercooling, vitrification and limited survival to −100° C. in the Alaskan beetle *Cucujus clavipes puniceus* larvae," J. Exp. Biol. 213(3): 502-509 (2010); Storey et al., "Freeze tolerance in animals," Physiol. Rev. 68: 27-84 (1988); Storey et al., "Biochemical adaptation for cold hardiness in insects," Phil. Trans. R. Soc. Lond. B326: 635-54 (1990); Walters et al., "Freeze tolerance in the Arctic Alaska Stonefly, *Nemoura arctica*," J. Exp. Biol. 212: 305-12 (2009a); Walters et al., "Cryoprotectant biosynthesis and the selective accumulation of threitol in the freeze tolerant Alaskan beetle, *Upis ceramboides*," J. Biol. Chem. 284: 16822-16831 (2009b); Walters et al., "A Non-protein thermal hysteresis-producing xylomannan antifreeze in the freeze-tolerant Alaskan beetle, *Upis ceramboides*," Proc. Natl. Acad. Sci. 106, 20210-20215 (2009c); Walters et al., "A thermal hysteresis-producing xylomannan glycolipid antifreeze associated with cold tolerance is found in diverse taxa," J. Comp. Physiol. B. 181(5): 631-40 (2011); Wang et al., "Antifreeze proteins of the beetle *Dendroides canadensis* enhance one another's activities," Biochemistry 44: 10305-10312 (2005); Worland et al., "Desiccation stress at subzero temperatures in polar terrestrial arthropods," J. Insect. Physiol. 49: 193-203 (2003); Zachariassen et al., "Nucleating agents in the haemolymph of insects tolerant to freezing," Nature 262: 285-87 (1976); and Zachariassen, "Physiology of cold tolerance in insects," Physiol. Rev. 65: 799-832 (1985).

Exemplary AFPs include AFPI (AFP type I), AFPIII (AFP type III) and/or AFGP. The AFP may be present in the cryopreservation composition in an amount of from, for example, about 0.001 to about 1 mg/mL, about 0.05 to about 0.5 mg/mL, or about 0.1 to about 0.75 mg/mL of composition, for each AFP present.

Once the cells have been contacted with the cryopreservation composition, the cells may then be frozen for cryopreservation. The cooling for cryopreservation may be conducted in any manner, and may use any additional materials to those described above.

For example, the cooling (freezing) protocol for cryopreservation may be any suitable type. Many types of cooling protocols are well known to practitioners in the art. The cooling protocol may include continuous rate cooling from the point of ice nucleation to −80° C. or any of the above disclosed cooling temperatures, with the rate of cooling depending on the characteristics of the cells/tissues being frozen. The cooling rate may be, for example, about −0.1° C. to about −10° C. per minute or about −1° C. to about −2° C. per minute. The cooling rate may be about −0.1 to about −9° C. per minute, about −0.1 to about −8° C. per minute, about −0.1 to about −7° C. per minute, about −0.1 to about −6° C. per minute, about −0.1 to about −5° C. per minute, about −0.1 to about −4° C. per minute, about −0.1 to about −3° C. per minute, about −0.1 to about −2° C. per minute, about 0.1 to about −1° C. per minute, about 0.1 to about −0.5° C. per minute, about −1 to about −2° C. per minute, about −1 to about −3° C. per minute, about −1 to about −4° C. per minute, about −1 to about −5° C. per minute, about −1 to about −6° C. per minute, about −1 to about −7° C. per minute, about −1 to about −8° C. per minute, about −1 to about −9° C. per minute, bout −1 to about −10° C. per minute, bout −2 to about −3° C. per minute, bout −2 to about −5° C. per minute, bout −2 to about −7° C. per minute, bout −2 to about −8° C. per minute, bout −2 to about −20° C. per minute, bout −4 to about −10° C. per minute, bout −4° per minute to about −8° C. per minute, bout −4 to about −6° C. per minute, bout −6 to about −10° C. per minute, bout −6 to about −9° C. per minute, bout −6 to about −8° C. per minute, bout −6 to about −7° C. per minute, bout −7 to about −10° C. per minute, bout −7 to about −9° C. per minute, bout −7 to about −8° C. per minute, bout −8 to about −9° C. per minute, or bout −9 to about −10° C. per minute. Once the cells are cooled to about −40° C. to −80° C. or lower by this continuous rate cooling, they may be transferred to liquid nitrogen or the vapor phase of liquid nitrogen for further cooling to the cryopreservation temperature, which is typically below the glass transition temperature of the freezing solution. The cell may be cooled to about −40° C. to about −75° C., about −45° C. to about −70° C., about −50° C. to about −60° C., about −55° C. to about −60° C., about −70° C. to about −80° C., about −75° C. to about −80° C., about −40° C. to about −45° C., about −40° C. to about −50° C., about −40° C. to about −60° C., about −50° C. to about −70° C., or about −50° C. to about −80° C. before further cooling to the cryopreservation temperature.

The warming protocol may involve a two-step warming procedure. In the two-step warming protocol, the cryopreserved cells (cryopreserved at the cryopreservation temperature) may be removed from the cryopreservation freezer. The cryopreserved cells are allowed to first slowly warm in a first environment in the first step of the two-step protocol. The environment is not required to undergo any special treatment or have any particular make-up, and any environment may be used. The environment may be a gaseous atmosphere, for example, air. To effect the slow warming of the first stage, the environment may be at a first warming temperature greater than the cryopreservation temperature. The first warming temperature may be near room temperature. For example, temperatures of 30° C. or less, such as about 15° C. to about 30° C., about 20° C. to about 25° C., or about 20° to about 30° C. may be used.

The second step of the two-step warming procedure involves thawing the cells rapidly in a second environment at a second warming temperature that is greater than the warming temperature used in the first warming step. The second warming temperature may be 32° C. or more, about 32° C. to about 50° C., about 35° C. to about 45° C., about 40° C. to about 50° C., about 45° C. to about 50° C., about 32° C. to about 40° C., about 35° C. to about 40° C., or about 37° C. Again, any suitable environment such as gas (air), liquid, or fluid bed may be used as the second environment. For example, a water bath at the warm temperature may be used to effect this rapid thawing.

Figure 5A:
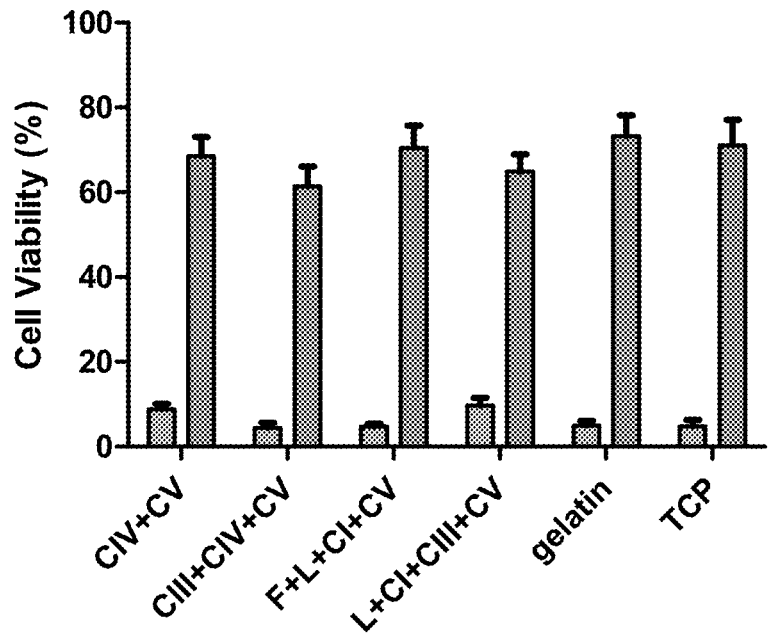
FIGS. 5A and 5B are bar graphs illustrating (A) cell viability and (B) DNA content (%) (i.e., cell retention) of adherent hMSCs on various substrates after cryopreservation and thawing via a single rapid thawing step or a two-step thawing protocol.
Figure 5B:
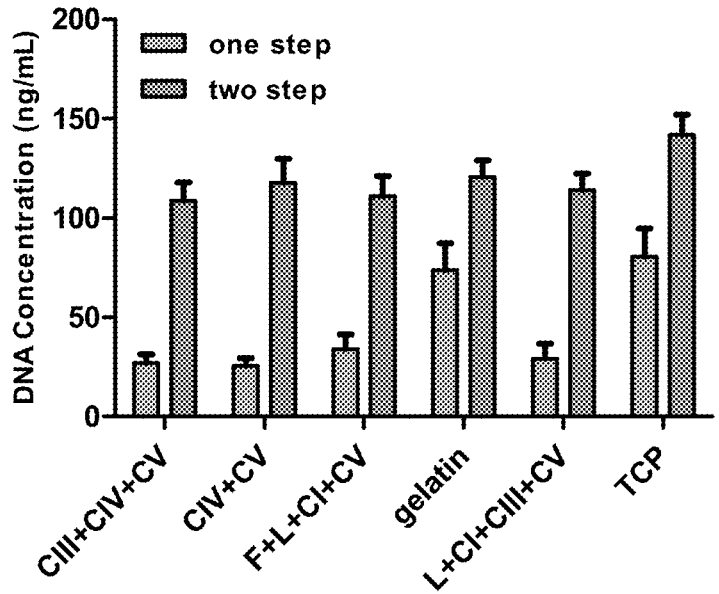

FIG. 5 illustrates that a two-step warming strategy improves cell viability and attachment. The addition of the ECM proteins promotes cell viability and attachment and ECM combinations that are effective may depend on cell type. The two-step warming strategy may be applied to all cell types cryopreserved as adherent cells on a fixed substrate.

Certain ECM components and/or certain combinations of ECM components may enhance the viability and retention of one type of cell but not another. Therefore, the present subject matter also relates to a method of identifying one or more ECM component that improves viability and retention of cells on a substrate after thawing the cells from a cryopreserved state. The method involves first selecting cells of a specific cell type, such as BCE cells or human mesenchymal stem cells. The method may also involve identifying ECM components that are known to be associated or produced by the selected cell type. Alternatively, known ECM components may be screened without prior knowledge of the specific ECM components associated with the selected cell type. Next, the substrate may be treated with the ECM components and various combinations of the ECM components, and the cells of the selected cell type may be plated on the variously treated substrates, followed by cryopreservation and subsequent thawing of the cells on the treated substrates, as described above. Once the cells have thawed, the cells may be evaluated for viability and retention to identify what ECM components or combinations of ECM components result in a cell viability (%) of 60% or more, such as 80% or more and a DNA content (%) of at least 80% for the selected cell type. Cell viability and retention may be evaluated according any known methods. Known methods for measuring cell viability (%) include viability assays such as fluorescent-based assays. Known methods for measuring DNA content (%) include cell proliferation assays, which may be used to provide an accurate measurement of cell number.

Cryoprotective agents that work best with the ECM components for the specific cell type may also be identified as the selection of the cryoprotectant compound can affect cell viability and retention after cryopreservation. For example, glycerol and DMSO promote the assembly of microtubules in vitro, whereas other cyroprotective agents such as propanediol, but not DMSO, depolymerize actin in oocytes. See, e.g., Vincent et al., "Effects of Cryoprotectants on Actin Filaments During the Cryopreservation of One-Cell Rabbit Embryos," Cryobiology, 27:9-23 (1990). In some cells, DMSO causes the disorganization of stress fibers and the formation of intracellular actin bundles. So, an important aspect of cryopreserving cells attached to substrates is the ability to retain the cells on the substrate after the rigors of freezing and thawing.

Examples are set forth herein below and are illustrative of different methods and conditions that may be utilized in practicing specific embodiments. Many alternatives, modifications, and variations will be apparent to those skilled in the art. Accordingly, the examples are intended to be illustrative only and not limiting.

EXAMPLES

Example 1

Cell Viability and Retention of Cells Cryopreserved on ECM Versus TCP

A differentiated cell line, BCE cells (BCE cell line, ATCC #CRL-2048) was maintained in Dulbecco's Modified Eagle's Medium (DMEM) with 10% fetal calf serum (FCS), 1.0 mM sodium pyruvate, and 4 mM glutamine, and penicillin (100 U)/streptomycin (100 µg/mL) at 37° C. with 5% carbon dioxide. The BCE cells were plated onto tissue culture plastic or onto a native BCE cell-derived ECM. To make the ECM, BCE cells were plated at a near confluent density (50,000 cells/well) in 96-well plates and left for 6 days in DMEM with 10% FCS and 82 µg/mL magnesium ascorbyl phosphate (from Wako Chemical). The ascorbic acid in the cell culture medium promoted the deposition and formation of an ECM. After 6 days, the cells were removed by the addition of 25 mM $NH_4OH$ in water followed by 3 washes with water. See, e.g., Roemer et al., "In Vitro Assay Systems for Inflammatory Cell-Mediated Damage to Interstitial Extracellular Matrix," In Vitro Toxicol., 7(2):75-81 (1994).

Plated BCE cells were then exposed to 2M DMSO and cryopreserved by placing the plates on ice and pretreating the cells with 0.5M mannitol to prepare the cells for exposure to the hyperosmotic environment anticipated when cryoprotectants, such as 2M DMSO, are added. After addition of the final concentration of cryoprotectant, the plates were cooled at controlled rates to −80° C., then placed at −130° C. The following controlled cooling rates were used: −0.2° C./min, −1.0° C./min, −10.0° C./min., and a modified −1.0° C./min. profile (MP) that included a nucleation step. After at least 24 hours of storage, the plates were warmed according to the two-step warming protocol in Campbell '531, supra. First the plates were placed at −20° C. for 30 minutes and then, the plates were placed at 37° C. for rapid thawing. As soon as the plates were thawed (no ice visually detectable), the plates were placed on ice and the wells were washed repeatedly with 0.5M mannitol in DMEM plus 10% FCS. After an additional wash of DMEM plus 10% FCS, the cells were left in DMEM (10% FCS) for 1 hour at 37° C. for recovery prior to assessment of cell viability and retention. After thawing, the cells were assessed for viability and cell retention using the ALAMAR BLUE® indicator and CYQUANT® assay, respectively.

Cell viability was determined using the ALAMAR BLUE® non-invasive metabolic indicator (from Trek Diagnostics). The ALAMAR BLUE® indicator is a fluorescent dye that measures the oxidation/reduction reactions within cells and thus is indicative of the overall viability of the cells after exposure to cryoprotective agents. The ALAMAR BLUE® indicator can be read using fluorescence or absorbance. A volume of 20 µl ALAMAR BLUE® indicator was added to the cells left in 200 µl of DMEM (10% FCS) after cryopreservation and the plate was incubated at 37° C. for 3 hours. Fluorescence from the ALAMAR BLUE® indicator was read in a fluorescent microplate reader (from Molecular Devices) at an excitation wavelength of 544 nm and an emission wavelength of 590 nm. The data was normalized against an untreated control. The values are presented as the means (+/−SEM) of 9-12 replicates.

The proportion of cells remaining in the well of the microtiter plate after cryopreservation (i.e., cell retention) was assessed by measuring the DNA content of the cells within each well via the CYQUANT® assay (from Molecular Probes). The DNA content was used as an indicator of cell number. The CYQUANT® assay uses a fluorescent dye to label nucleic acids, which are then measured using a fluorescent microplate reader with an excitation wavelength of 485 nm and an emission wavelength of 538 nm. RNAse A (from Sigma) was also used to eliminate the variable amount of RNA within individual cells and thereby provide a direct measure of the DNA content. The data was normalized against untreated control cells and represents the mean (+/−SEM) of 9-12 replicates.

As illustrated in FIG. 1, cell viability was considerably improved when the cells were plated on their own native ECM rather than TCP regardless of the cooling rate used ($p<0.001$). Cell retention for all cooling rates except −10.0° C./min was equivalent or better when cells were plated on an ECM versus TCP. At −10.0° C./min, however, there was a significant improvement in cell retention when the cells were plated on their ECM rather than TCP ($p<0.0001$). FIG. 1 further illustrates that lower cooling rates generally provided better viability and attachment over higher cooling rates ($p<0.001$). Although the presence of an ECM improved cell viability during cryopreservation across all cooling rates, cell retention was enhanced by the presence of an ECM during cryopreservation at higher cooling rates. At lower cooling rates, cell retention of cells plated on an ECM and TCP was equivalent. One possible explanation is that ECM proteins such as vitronectin, which are present in the serum used in the cell culture medium, produced a rudimentary matrix, thereby providing a framework for anchorage of the cells during cryopreservation. Due to this possibility the subsequent examples (2-4) were performed serum-free.

The presence of a fully formed and organized ECM provides a surface that more closely resembles the cells' native environment. Therefore, cell attachment is impacted less by the cryopreservation process. Additionally, the composition of the ECM can influence the ability of the cells to remain attached during cryopreservation. Furthermore, by cryopreserving the cells with an ECM, the cells are in a configuration that is more conducive to their overall health and may improve their endurance and resilience in response to freezing temperatures.

Example 2

Cell Viability and Retention of BCE Cells Cryopreserved with Various Combinations of ECM Components BCE cells (BCE cell line, ATCC #CRL-2048) were maintained in Dulbecco's Modified Eagle's Medium (DMEM) with 10% fetal calf serum (FCS), 1.0 mM sodium pyruvate, and 4 mM glutamine, and penicillin (100 U)/streptomycin (100 μg/mL) at 37° C. with 5% carbon dioxide.

Optimal concentrations of five ECM components—fibronectin, laminin, collagen I, collagen III, collagen IV, and collagen V—were determined and then evaluated either as a single component or in combination with one or more other components. The ECM proteins were obtained from commercial sources and concentrations of ~1-10 μg/mL were used to treat microtiter plates prior to cell plating. Individual wells were treated with various concentrations of ECM proteins in phosphate-buffered saline (PBS) and left for 2 hours at 37° C. followed by a 1 hour incubation at 37° C. with 1% bovine serum albumen (BSA) to block unoccupied binding sites according to methods known in the art. See, e.g., Underwood, "The Effect of Extracellular Matrix Molecules on the In Vitro Behavior of Bovine Endothelial Cells," Exp. Cell. Res. 205:311-319 (1993). Wells were rinsed with culture medium without serum and then left in medium until cells were plated.

The cells were cryopreserved and subsequently thawed as described above in Example 1. Cell viability and retention were evaluated using the ALAMAR BLUE® indicator and CYQUANT® assay, as in Example 1. Evaluation of cell viability and continued cell attachment after cryopreservation was performed using two cryoprotectants, DMSO, and 1,2-Propanediol (PD). Cells were plated in wells treated with the various ECM combinations at a cell density of 80,000 cells/well. The results presented in FIGS. 2 and 3 are from cells that were cryopreserved as a monolayer with 2.0M DMSO in the vehicle solution Hepes-buffered saline (HBSI) (275 mM NaCl, 25 mM Hepes). Similar results using different ECM combinations were observed using PD as the cryoprotective agent.

As shown in FIGS. 2 and 3, several combinations of ECM components demonstrated excellent viability and attachment. The cell viability percent and DNA content, which is indicative of cell number, were calculated based on separate untreated control cells plated at the same time as the treated cells. Statistical analysis of the data did not identify any one ECM component combination as the most significant. Rather, groups of ECM combinations were considered significantly better than the rest and were dependent on the cryoprotective agent used ($p<0.01$). Trends that were noted included better viability and attachment occurring with more complex ECM component mixtures (4 or more). FIG. 2 illustrates that ECM protein pairs greatly improved cell viability after cryopreservation and subsequent thawing. The best combinations included fibronectin and collagen I for viability, or fibronectin and collagen V for attachment with laminin contributing the least to improve viability and attachment of the BCE cells. Several combinations of four ECM components (F+L+CI+CIV, F+CIII+CIV+CV, and CI+CIII+CIV+CV) resulted in approximately 100% cell survival and adherence post-cryopreservation.

FIG. 3 illustrates that the presence of even a single ECM protein improved cell attachment over TCP alone. Cell attachment was >80% for all the ECM combinations tested including a matrix that was laid down by the BCE cells. An overall improvement in cell attachment was observed by cryopreserving the cells with at least one ECM component.

Example 3

Cell Viability and Retention of hMSCs Cryopreserved with Various Combinations of ECM Components Human bone-marrow derived mesenchymal stem cells were maintained in DMEM/F12 medium with 10% FCS, non-essential amino acids, 2 mM Glutamax, and penicillin (50 U)/streptomycin (50 μg/mL) at 37° C. with 5% carbon dioxide.

Initial experiments evaluated ECM components—fibronectin, laminin, collagen I, collagen III, collagen IV, and collagen V—individually to determine optimal concentrations. Then, pairs of proteins were examined using concentrations established with the individual proteins. Further combinations of three or four proteins were chosen and examined based on results obtained with the individual proteins and various pairs of proteins. The ECM proteins were obtained from commercial sources and concentrations of ~1-10 μg/mL were used to treat microtiter plates prior to cell plating. Individual wells were treated with various concentrations of ECM proteins in phosphate-buffered saline (PBS) and left for 2 hours at 37° C. followed by a 1 hour incubation at 37° C. with 1% bovine serum albumen (BSA) to block unoccupied binding sites. Wells were rinsed with culture medium without serum and then left in medium until cells were plated.

The cells were cryopreserved and subsequently thawed as described above in Example 1. After thawing, viability was measured and compared with cells attached to either TCP or gelatin, which is used routinely for regular growth and maintenance of hMSC, to determine which ECM components provide the most support for continued viability and attachment of cells during cryopreservation. In these experiments, percent cell viability was calculated based on the viability of the cells in each well prior to being cryopreserved. Cell viability and retention were evaluated using the ALAMAR BLUE® indicator and CYQUANT® assay, as in Example 1.

While it was evident that combinations of more than one ECM protein improved cell viability for BCE cells, this was not necessarily the case for hMSC. Single ECM components improved viability of hMSCs to a similar degree as did combinations of 2 or more ECM components. Combinations of 4 or more ECM proteins worked best for BCE cells, but hMSCs had definite preferences with regard to the combinations that produced the best viability. Two combinations of ECM components produced viability that was >70%, F+L+CI+CV and CIV+CV. Another group of combinations produced viability of >60% and included: F+L+CV, L+CIV+CV, CIII+CIV+CV, F+L+CIV+CV, F+CI+CIV+CV, F+CIII+CIV+CV, and L+CI+CIII+CV. Interestingly, gelatin that is usually used for hMSC cell culture did not promote cell viability post-cryopreservation and thawing. This demonstrates that established methods of substrate treatment for specific cell type culture do not necessarily work for cryopreservation. This was also observed when matricellular proteins were included (see Example 4). In general, the presence of at least one ECM protein improved hMSC viability after cryopreservation. Those combinations that demonstrated the best viability tended to include fibronectin, collagen IV and/or collagen V in their mixture.

Example 4

Figure 6:
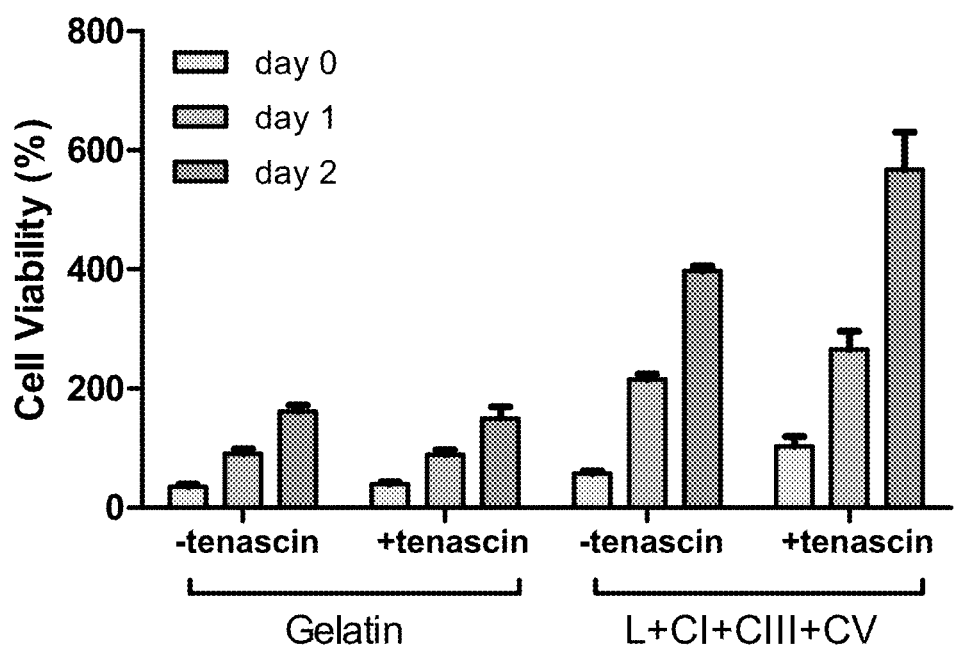
FIG. 6 is a bar graph illustrating cell viability of adherent hMSCs after cryopreservation on gelatin or the ECM combination of laminin, collagen I, collagen III, and collagen V with or without the matricellular protein, Tenascin X.

Viability of hMSCs after Cryopreservation with the Matricellular Protein, Tenascin X Human bone marrow-derive mesenchymal stem cells were plated on gelatin or the ECM combination of laminin, collagen I, collagen III, and collagen V. A matricellular protein, Tenascin X at a concentration of 500 ng/mL, was included for the samples indicated in FIG. 6 at the time the cells were plated. The cells were cryopreserved in 1M DMSO with 2.5% chondroitin sulfate, and subsequently thawed as described in Example 1. Cell viability was measured after thawing and normalized to an untreated control.

The addition of tenascin X promoted improvement in cell viability (100%) over the presence of the ECM alone (57%) and the overall viability of hMSCs on the ECM±tenascin X was better than when the cells were plated on gelatin ($p<0.05$, FIG. 1). Interestingly, tenascin X did not demonstrate any improvement when used with gelatin as compared with the ECM combination, probably because gelatin is a processed form of collagen whereas the ECM components used in the combination were all produced as native proteins. This further emphasizes that established methods of substrate treatment for specific cell type culture may not necessarily work during cryopreservation of adherent cells.

The results presented here for a differentiated cell line and mesenchymal stem cells have demonstrated that addition of ECM components improves the viability and maintains the attachment of cells adhered to a multiwell plate after cryopreservation. Differences were observed between the two types of cells emphasizing the critical role that the ECM can play in the health and maintenance of cells in vitro and in vivo. This is especially important for the stem cells as the ECM can influence their ability to differentiate and into what cell lineages they will go. These results also demonstrated that the composition of the ECM influences the cells and their ability to survive cryopreservation as an adherent population.

It will be appreciated that various of the above-disclosed and other features and functions, or alternatives thereof, may be desirably combined into many other different systems or applications. Also, various presently unforeseen or unanticipated alternatives, modifications, variations or improvements therein may be subsequently made by those skilled in the art, and are also intended to be encompassed by the following claims.

What is claimed is:

1. A method for cryopreservation of adherent cells on a substrate comprising:
   treating a substrate with a combination of extracellular matrix components prior to plating the cells on the substrate and/or adding one or more matricellular proteins to the substrate or to the cells in a cell culture medium;
   plating the cells on the substrate; and
   cryopreserving the cells on the substrate by cooling the cells to a cryopreservation temperature;
   wherein
      the one or more matricellular proteins is selected from the group consisting of tenascin-C, tenascin-X, periostin, CCN-1, osteopontin, and mixtures thereof; and
      the combination of extracellular matrix components is:
         (i) fibronectin, laminin, collagen I, and collagen IV,
         (ii) fibronectin, collagen III, collagen IV, and collagen V, or
         (iii) collagen I, collagen III, collagen IV, and collagen V.

2. The method according to claim 1, further comprising subsequently thawing the cells by:
   first warming the cells from the cryopreservation temperature by exposing the substrate containing the cells to a first environment having a first warming temperature greater than the cryopreservation temperature; and then
   further warming the cells from the first warming temperature by exposing the cells to a second environment having a second warming temperature that is greater than the first warming temperature.

3. The method according to claim 2, wherein:
the cryopreservation temperature is at least −30° C.;
the first warming temperature is greater than −30° C. and less than 30° C.; and
the second warming temperature is at least 32° C.

4. The method according to claim 1, wherein the cells are bovine corneal endothelial cells.

5. The method according to claim 1, wherein the cells are human mesenchymal stem cells.

6. A method for cryopreservation of adherent cells on a substrate comprising:
adding one or more matricellular proteins to the substrate or to the cells in a cell culture medium, and optionally treating the substrate with at least one extracellular matrix component;
plating the cells on the substrate; and
cryopreserving the cells on the substrate by cooling the cells to a cryopreservation temperature;
wherein the one or more matricellular proteins is selected from the group consisting of actin-binding proteins, thrombospondin-1, tenascin-C, tenascin-X, SPARC, periostin, CCN-1, and osteopontin; and
wherein the cells are human mesenchymal stem cells.

7. The method according to claim 6, wherein the at least one extracellular matrix component is selected from the group consisting of fibronectin, laminin, collagen I, collagen II, collagen IV, collagen V, and vitronectin.

8. The method according to claim 7, wherein the at least one extracellular matrix component comprises at least fibronectin, collagen IV, and collagen V.

9. A method for cryopreservation of adherent cells on a substrate comprising:
adding at least one matricellular protein to a substrate or to the cells in a cell culture medium, and optionally treating the substrate with at least one extracellular matrix component;
plating the cells on the substrate; and
cryopreserving the cells on the substrate by cooling the cells to a cryopreservation temperature;
wherein the at least one matricellular protein is selected from the group consisting of actin-binding proteins, thrombospondin-1, tenascin-C, tenascin-X, periostin, CCN-1, and osteopontin.

10. The method according to claim 9, wherein the addition of the at least one matricellular protein to the substrate or to the cells is separate from any natural production of a matricellular protein by the cells.

11. The method according to claim 9, wherein the at least one extracellular matrix component is selected from the group consisting of fibronectin, laminin, collagen I, collagen II, collagen IV, collagen V, and vitronectin.

12. The method according to claim 9, further comprising subsequently thawing the cells by:
first warming the cells from the cryopreservation temperature by exposing the substrate containing the cells to a first environment having a first warming temperature greater than the cryopreservation temperature; and then
further warming the cells from the first warming temperature by exposing the cells to a second environment having a second warming temperature that is greater than the first warming temperature.

13. The method according to claim 12, wherein:
the cryopreservation temperature is at least −30° C.;
the first warming temperature is greater than −30° C. and less than 30° C.; and
the second warming temperature is at least 32° C.

14. The method according to claim 9, wherein the cells are human mesenchymal stem cells or bovine corneal endothelial cells.

15. A method for cryopreservation of adherent cells on a substrate comprising:
treating a substrate with a combination of extracellular matrix components and/or adding at least one matricellular protein to the substrate or to the cells in a cell culture medium;
plating the cells on the substrate; and
cryopreserving the cells on the substrate by cooling the cells to a cryopreservation temperature;
wherein
the treatment of the substrate with the combination of extracellular matrix components is in addition to any natural production of an extracellular matrix component by the cells, and the combination of extracellular matrix components is:
(i) fibronectin, laminin, collagen I and collagen IV,
(ii) fibronectin, collagen III, collagen IV, and collagen V, or
(iii) collagen I, collagen III, collagen IV, and collagen V; and
the at least one matricellular protein is selected from the group consisting of tenascin-C, tenascin-X, periostin, CCN-1, osteopontin, and mixtures thereof.

16. The method according to claim 15, further comprising subsequently thawing the cells by:
first warming the cells from the cryopreservation temperature by exposing the substrate containing the cells to a first environment having a first warming temperature greater than the cryopreservation temperature; and then
further warming the cells from the first warming temperature by exposing the cells to a second environment having a second warming temperature that is greater than the first warming temperature.

17. The method according to claim 16, wherein:
the cryopreservation temperature is at least −30° C.;
the first warming temperature is greater than −30° C. and less than 30° C.; and
the second warming temperature is at least 32° C.

18. The method according to claim 15, wherein the cells are human mesenchymal stem cells or bovine corneal endothelial cells.

* * * * *